(12) United States Patent
Ivory et al.

(10) Patent No.: US 8,986,530 B2
(45) Date of Patent: Mar. 24, 2015

(54) SAMPLE ANALYSIS SYSTEMS, DEVICES, AND ASSOCIATED METHODS OF OPERATION

(75) Inventors: Cornelius F. Ivory, Pullman, WA (US); Dan M. Leatzow, Kalispell, MT (US)

(73) Assignee: Washington State University, Pullman, WA (US)

( * ) Notice: Subject to any disclaimer, the term of this patent is extended or adjusted under 35 U.S.C. 154(b) by 366 days.

(21) Appl. No.: 13/445,228

(22) Filed: Apr. 12, 2012

(65) Prior Publication Data

US 2013/0175173 A1 Jul. 11, 2013

Related U.S. Application Data

(63) Continuation-in-part of application No. 13/371,253, filed on Feb. 10, 2012.

(60) Provisional application No. 61/584,532, filed on Jan. 9, 2012.

(51) Int. Cl.
*G01N 27/447* (2006.01)

(52) U.S. Cl.
CPC .............................. *G01N 27/44717* (2013.01)
USPC ............ 204/549; 204/542; 204/603; 204/645

(58) Field of Classification Search
CPC .............................. G01N 27/447; B01D 57/02
USPC .................. 204/450–455, 549, 601–605, 645
See application file for complete search history.

(56) References Cited

PUBLICATIONS

Emrich, et al. "Microfabricated Two-Dimensional Electrophoresis Device for Differential Protein Expression Profiling", Analytical Chemistry, vol. 79, No. 19, Oct. 2007, p. 7360-7366.*

Jubery, et al. "Preconcentration of Cardiac Proteins in a Microfluidic Device", Paper IMECE2009-10772; vol. 12, Part B, Micro and Nano Systems, Proceedings of the ASME 2009 International Mechanical Engineering Congress & Exposition, Nov. 13-19, 2009, p. 613-617.*
Bottenus, et al. "Preconcentration and detection of the phosphorylated forms of cardiac troponin I in a cascade microchip by cationic isotachophoresis", Lab on a Chip, vol. 11, No. 22, Nov. 2011, p. 3793-3801.*
An et al., "Selective enrichment and ultrasensitive identification of trace peptides in proteome analysis using transient capillary isotachophoresis/zone electrophoresis coupled with nano-ESI-MS," Electrophoresis, 27, pp. 3599-3608, 2006.
Belligundu, Sunil and Shiakolas, Panayiotis S., "Study on two-stage hot embossing microreplication: silicon to polymer to polymer," J. Microlith, Microfab., Microsyst, 5(2), 021103, pp. 1537-1646, Apr.-Jun. 2007.
Chen, et al., "Fabrication and characterizatoin of poly(methyl methacrylate) microchannels by in situ polymerization with a novel metal template," Electrophoresis, 24, pp. 3246-3252, 2003.
Chen et al., "Fabrication of poly(methyl methacrylate) microfluidic chips by redox-initiated polymerization," Electrophoresis, 28, pp. 2897-2903, 2007.

(Continued)

*Primary Examiner* — J. Christopher Ball
(74) *Attorney, Agent, or Firm* — Liang IP, PLLC

(57) ABSTRACT

Embodiments of analysis systems, electrophoresis devices, and associated methods of analysis are described herein. In one embodiment, a method of analyzing a sample containing an electrolyte includes sequentially introducing a leading electrolyte, a sample electrolyte, and a trailing electrolyte into a extraction channel carried by a substrate. The extraction channel has a constriction in cross-sectional area. The method also includes applying an electrical field to separate components of the sample electrolyte into stacks and to concentrate the separated components by forcing the sample electrolyte to migrate through the constriction in the extraction channel. Thereafter, the applied electrical field is removed and the separated and concentrated components of the sample are detected in a detection channel carried by the substrate.

20 Claims, 9 Drawing Sheets

(56) References Cited

PUBLICATIONS

Chen, et al., "Fabrication, modification, and application of poly(methyl methacrylate) microfluidic chips," Electrophoresis, 29, pp. 1801-1814, 2008.

Chen, et al., "Fabrication of PMMA CE microchips by infrared-assisted polymerization," Electrophoresis 29, pp. 4922-4927, 2008.

Das, Champak and Fan, Z. Hugh, "Effects of separation length and voltage on isoelectric focusing in a plastic microfluidic device," Electrophoresis 27, pp. 3619-3626, 2006.

Davis, et al., "Capillary and Microfludic Gradient Elution Isotachophoresis Coupled to Capillary Zone Electrophoresis for Femtomolar Amino Acid Detection Limits," Analytical Chemistry, vol. 81, No. 13, pp. 5452-5459, Jul. 1, 2009.

Dittrich, Petra S. and Manz, Andreas, "Lab-on-a-chip: microfluidics in drug discovery," vol. 5, Nature Publishing Group, pp. 210-218, Reviews, Nature Publishing Group, Mar. 2006.

Fang, et al., "Application of capillary isotachophoresis-based multidimensional separations coupled with electrospray ionizaton-tandem mass spectrometry for characterization of mouse brain mitochondrial proteome," Electrophoresis, vol. 29, pp. 2215-2223, 2008.

Harrison, et al., "Micromachining a Miniaturized Capillary Electrophoresis-Based Chemical Analysis System on a Chip," American Association for the Advancement of Science, vol. 261, No. 5123, pp. 895-897, Aug. 13, 1993.

Hirokawa, et al., "Analysis of a dilute sample by capillary zone electrophoresis with isotachophoretic preconcentration," Journal of Chromatography, vol. 634, Issue 1, pp. 101-106, 1993.

Hsu, Yi-Chu and Chen, Tang-Yuan, "Applying Taguchi methods for solvent-assisted PMMA bonding technique for static and dynamic-TAS devices," Biomed Microdevices, vol. 9, pp. 513-522, 2007.

Kim, Joohan and Xu, Xianfan, "Excimer laser fabrication of polymer microfluidic devices," Journal of Laser Applicatons, vol. 15, No. 4, pp. 255-260, Nov. 2003.

Koesdjojo, et al., "Fabrication of a Microfluidic System for Capillary Electrophoresis Using a Two-Stage Embossing Technique and Solvent Welding on Poly(methyl methacrylate) with Water as a Sacrificial Layer," Analytical Chemistry, vol. 80, No. 7, pp. 2311-2318, Apr. 1, 2008.

Liu, et al., "Isotachophoresis preconcentration integrated microfluidic chip for highly sensitive genotyping of the hepatitis B virus," Journal of Chromatography B, vol. 844, pp. 32-38, 2006.

Liu, et al., "Double-column fixation for type C fractures of the distal humerus in the elderly," Journal of Shoulder and Elbow Surgery, 18, pp. 646-651, 2009.

Lu, et al., "Packaging of Microfluidic Chips via Interstitial Bonding Technique," Research Express@NCKU, vol. 9, Issue 7, 5 pages, Jul. 10, 2009.

Manz, et al., "Planar chips technology for miniaturization and integration of separation techniques into monitoring systems," Journal of Chromatography, 593, pp. 253-258, 1992.

Qi, et al., "Microfluidic devices fabricated in poly(methyl methacrylate) using hot-embossing with integrated sampling capillary and fiber optics for fluorescence detection," Lab Chip, 2, pp. 88-95, Mar. 28, 2002.

Qu, et al., "Poly(methyl methacrylate) CE microchips replicated from poly(dimethylsiloxane) templates for the determination of cations," Electrophoresis 27, pp. 4910-4918, 2006.

Xia, Younan and Whitesides, George M., "Soft Lithography," Annu. Rev. Mater. Sci. 28, pp. 153-184, 1998.

Xu, et al, "Fabrication of poly(methyl methacrylate) capillary electrophoresis microchips by in situ surface polymerization," Lab Chip, 6, pp. 145-148, 2006.

Xu, et al., "Sensitive profiling of biogenic amines in urine using CE with transient isotachophoretic preconcentration," J. Sep. Sci., 32, pp. 4143-4147, 2009.

Yan, et al., "In-line preconcentration of oxidized and reduced glutathione in capillary zone electrophoresis using transient isotachophoresis under strong counter-electroosmotic flow," Journal of Chromatography A, 1216, pp. 8665-8670, 2009.

Zhu, et al., "Study of PMMA thermal bonding," Microsyst Technol. 13, pp. 403-407, 2007.

Becker, Holger and Locascio, Laurie, E., "Polymer microfluidic devices," Talanta 56, pp. 267-287, 2002.

Brister, Paul C. and Weston, Kenneth, D., "Patterned Solvent Delivery and Etching for the Fabrication of Plastic Microfluidic Devices," Analytical Chemistry, vol. 77, No. 22, pp. 7478-7482, Nov. 15, 2005.

Brown, et al., "Fabrication and characterization of poly(methylmethacrylate) microfluidic devices bonded using surface modifications and solvents," Lab Chip, 6, pp. 66-73, 2006.

Brown, Robert B. and Audet, Julie, "Sampling Efficiency of a Single-Cell Capillary Electrophoresis System," Cytometry Part A, 71A, pp. 882-888, 2007.

Cheng, et al., "Direct-write laser micromachining and universal surface modification of PMMA for device development," Sensors and Actuators B, 99, pp. 186-196, 2004.

Cui, et al., "Isoelectric Focusing in a Poly(dimethylsiloxane) Microfluidic Chip," Analytical Chemistry, vol. 77, No. 5, pp. 1303-1309, Mar. 1, 2005.

Cui, et al., "Isotachophoresis of proteins in a networked microfluidic chip: Experiment and 2-D simulation," Electrophoresis, 28, pp. 1138-1145, 2007.

Cui, et al., "Automated Electric Valve for Electrokinetic Separation in a Networked Microfluidic Chip," Analytical Chemistry, vol. 79, No. 4, pp. 1456-1465, Feb. 15, 2007.

Kelly, Ryan T. and Woolley, Adam, T., "Thermal Bonding of Polymeric Capillary Electrophoresis Microdevices in Water," Analytical Chemistry, vol. 75, No. 8, pp. 1941-1945, Apr. 15, 2003.

Klank, et al., "Co2-laser micromachining and back-end processing for rapid production of PMMA-based microfluidic systems," Lab Chip, 2, pp. 242-246, 2002.

Koesdjojo, et al., "Techniques for Microfabrication of Polymeric-Based Microchips from an SU-8 Master with Temperature-Assisted Vaporized Organic Solvent Bonding," Analytical Chemistry, vol. 81, No. 4, pp. 1652-1659, Feb. 15, 2009.

Kaniansky, et al., "Capillary Electrophoresis Separations on a Planar Chip with the Column-Coupling Configuration of the Separation Channels," Analytical Chemistry, vol. 72, No. 15, pp. 3596-3604, Aug. 1, 2000.

Krivankova, Ludmila and Bocek, Petr, "Synergism of capillary isotachophoresis and capillary zone electrophoresis," Journal of Chromatography B, 689, pp. 13-34, 1997.

Lei, et al., "Microwave bonding of polymer-based substrates for potential encapsulated micro/nanofluidic device fabrication," Sensors and Actuators A 114, pp. 340-346, 2004.

Mair, et al., "Room-Temperature Bonding for Plastic High-Pressure Microfluidic Chips," Analytical Chemistry, vol. 79, No. 13, pp. 5097-5102, Jul. 1, 2007.

Metwalli, et al., "Surface characterizations of mono-, di-, and tri-aminosilane treated glass substrates," Journal of Colloid and Interface Science, 298, pp. 825-831, 2006.

Ng, et al., "Thermally activated solvent bonding of polymers," Microsyst Technol. 14, pp. 753-759, 2008.

Peeni, et al., "Sacrificial layer microfluidic device fabrication methods," Electrophoresis, 27, pp. 4888-4895, 2006.

Shah, et al., "Capillarity Induced Solvent-Actuated Bonding of Polymeric Microfluidic Devices," Analytical Chemistry, vol. 78, No. 10, pp. 3348-3353, May 15, 2006.

Sun et al., "Rapid prototyping of poly(methyl methacrylate) microfluidic systems using solvent imprinting and bonding," Journal of Chromatography A, 1162, pp. 162-166, 2007.

Truckenmuller, et al., "Micro ultrasonic welding: joining of chemically inert polymer microparts for single material fluidic components and systems," Microsyst Technol. 12, pp. 1027-1029, 2006.

Urbanek, et al., "Determination of trace cationic impurities in butylmethylimidazolium-based ionic liquids: From transient to comprehensive single-capillary counterflow isotachophoresis-zone electrophoresis," Electrophoresis, 27, pp. 4859-4871, 2006.

Vreeland, et al., "Tandem Isotachophoresis-Zone Electgrophoresis via Base-Mediated Destacking for Increased Detection Sensitivity in Microfluidic Systems," Analytical Chemistry, vol. 75, No. 13, pp. 3059-3065, Jul. 1, 2003.

(56) References Cited

OTHER PUBLICATIONS

Wainright, et al., "Sample pre-concentration by isotachophoresis in microfluidic devices," Journal of Chromatography A, 979, pp. 69-80, 2002.

Xiong, et al., "Base Stacking: pH-Mediated On-Column Sample Concentration for Capillary DNA Sequencing," Analytical Chemistry, vol. 70, No. 17, pp. 3605-3611, Sep. 1, 1998.

Xu, et al., "Room-Temperature Imprinting Method for Plastic Microchannel Fabrication," Analytical Chemistry, vol. 72, No. 8, pp. 1930-1933, Apr. 15, 2000.

Yussuf, et al., "Sealing of polymeric-microfluidic devices by using high frequency electromagnetic field and screen printing technique," Journal of Materials Processing Technology, 189, pp. 401-408, 2007.

Becker, Holger and Garnter, Claudia, "Polymer microfabrication methods for microfluidic analytical applications," Electrophoresis, 21, pp. 12-26, 2000.

Becker, Holger and Garnter, Claudia, "Polymer microfabrication technologies for microfluidic systems," Anal. Bioanal Chem, 390, pp. 89-111, 2008.

Chen, Yu-hung and Chen, Shu-Hui, "Analysis of DNA fragments by microchip electrophoresis fabricated on poly(methyl methacrylate) substrates using a wire-imprinting method," Electrophoresis, 21, pp. 165-170, 2000.

Chen et al., "Palladium Film Decoupler for Amperometric Detection in Electrophoresis Chips," Analytical Chemistry, vol. 73, No. 4, pp. 758-762, Feb. 15, 2001.

Del Campo et al., "Patterned Surfaces with Pillars with Controlled 3D Tip Geometry Mimicking Bioattachment Devices," Advanced Materials, 19, pp. 1973-1977, 2007.

Dolnik, et al., "Capillary electrophoresis on microchip," Electrophoresis, 21, pp. 41-54, 2000.

Duffy, et al., "Rapid Prototyping of Microfluidic Systems in Poly(dimethylsiloxane)," Analytical Chemistry, vol. 70, No. 23, pp. 4974-4984, Dec. 1, 1998.

El-Ali, et al., "Cells on chips," Nature Publishing Group, vol. 442, pp. 403-411, Jul. 27, 2006.

Esch, et al., "Influence of master fabrication techniques on the characteristics of embossed microfluidic channels," Lab Chip, 3, pp. 121-127, 2003.

Ferguson, et al., "Integrated Microfluidic Electrochemical DNA Sensor," Analytical Chemistry, vol. 81, No. 15, pp. 6503-6508, Aug. 1, 2009.

Fiorini, et al., "Fabrication of thermoset polyester microfluidic devices and embossing masters using rapid prototyped polydimethylsiloxane molds," Lab Chip, 3, pp. 158-163, 2003.

Fuentes, Herman V. and Woolley, Adam T., "Phase-Changing Sacrificial Layer Fabrication of Multilayer Polymer Microfluidic Devices," Analytical Chemistry, vol. 80, No. 1, pp. 333-359, Jan. 1, 2008.

Kelly, et al., "Phase-Changing Sacrificial Materials for Solvent Bonding of High-Performance Polymeric Capillary Electrophoresis Microchips," Analytical Chemistry, vol. 77, No. 11, pp. 3536-3541, Jun. 1, 2005.

Koerner, et al., "Epoxy resins as stamps for hot embossing of microstructures and microfluidic channels," Sensors and Actuators B, 107, pp. 632-639, 2005.

Kraly, et al., "Review: Microfluidic applications in metabolomics and metabolic profiling," Analytica Chimica Acta 653, pp. 23-25, 2009.

Lion et al., "Microfludic Systems in Proteomics," Electrophoresis, 24, pp. 3533-3562, 2003.

Martynova, et al., "Fabrication of Plastic Microfluid Channels by Imprinting Methods," Analytical Chemistry, vol. 69, No. 23, pp. 4783-4789, Dec. 1, 1997.

McCormick, et al., "Microchannel Electrophoretic Separations of DNA in Injection-Molded Plastic Substrates," Analytical Chemistry, vol. 69, No. 14, pp. 2626-2630, Jul. 15, 1997.

Muck, et al., "Fabrication of Poly(methyl methacrylate) Microfluidic Chips by Atmospheric Molding," Analytical Chemistry, vol. 76, No. 8, Apr. 15, 2004.

Narasimhan, Jagannathan and Papautsky, Ian, "Polymer embossing tools for rapid protyping of plastic microfluidic devices," Journal of Micromechanics and Microengineering, 14, 96, 9 pages, 2004.

Pamme, Nicole, "Continuous flow separations in microfluidic devices," Lab Chip, 7, pp. 1644-1659, 2007.

Mairhofer, et al., "Microfluidic Systems for Pathogen Sensing: A Review," Sensors, 9, pp. 4804-4823, Jun. 17, 2009.

Sabounchi, et al., "Sample concentration and impedance detection on a microfluidic polymer chip," Biomed Microdevices, 10, pp. 661-670, May 17, 2008.

Shadpour, et al., "Physiochemical properties of various polymer substrates and their effects on microchip electrophoresis performance," Journal of Chromatography A, 1111, pp. 238-251, 2006.

Szantai, Eszter and Guttman, Andras, "Genotyping with microfluidic devices," Electrophoresis, 27, pp. 4896-4903, 2006.

Tsao, Chia-Wen and Devoe, Don L., "Bonding of thermoplastic polymer microfluidics," Microfluid Nanofluid, 6, pp. 1-16, 2009.

Wang, Shau-Chun and Morris, Michael, D., "Plastic Microchip Electrophoresis with Analyte Velocity Modulation Application to Fluorescence Background Rejection," Analytical Chemistry, vol. 72, No. 7, pp. 1448-1452, Apr. 1, 2000.

Office Action in U.S. Appl. No. 13/371,265 issued Nov. 14, 2014, 13 pages.

* cited by examiner

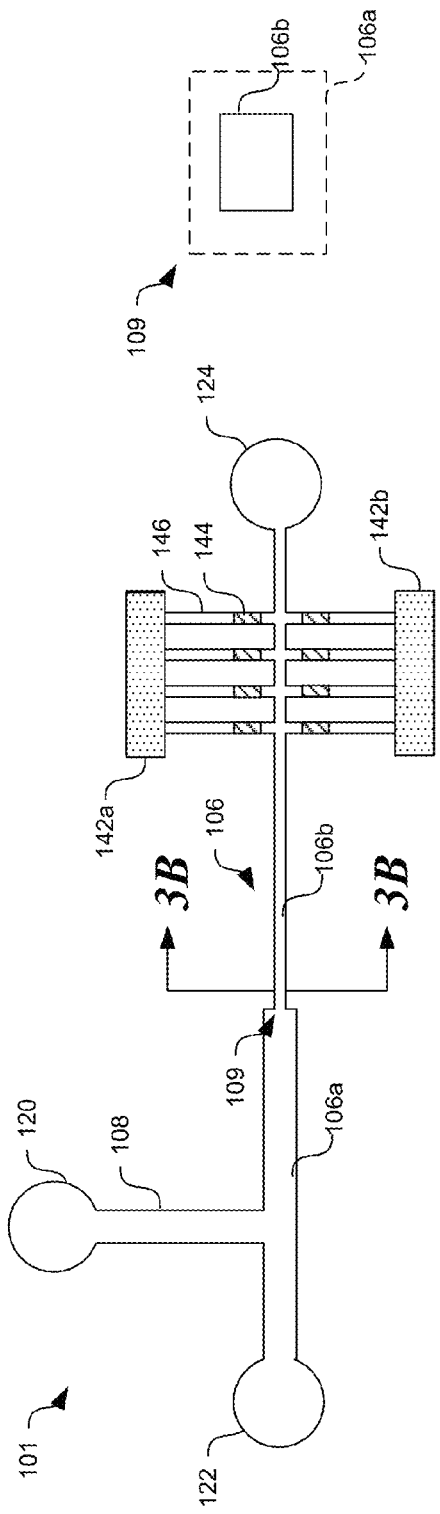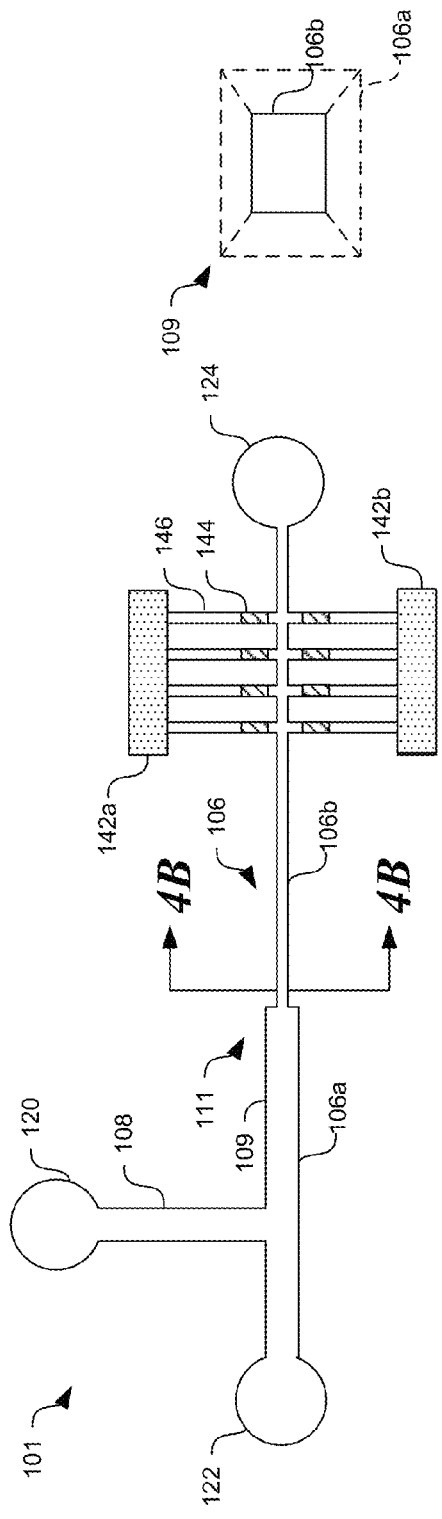

SAMPLE ANALYSIS SYSTEMS, DEVICES, AND ASSOCIATED METHODS OF OPERATION

CROSS-REFERENCE TO RELATED APPLICATION(S)

This application claims priority to U.S. Provisional Application No. 61/584,532, entitled "CONCENTRATION OF LOW ABUNDANCE COMPOUNDS," filed on Jan. 9, 2012, and U.S. application Ser. No. 13/371,253, entitled "ELECTROPHORESIS SYSTEMS, DEVICES, AND ASSOCIATED METHODS OF ANALYSIS," filed on Feb. 10, 2012.

BACKGROUND

Analyzing samples with dilute components may be challenging because target concentrations may be below detection limits of conventional diagnostic techniques. For example, cardiac troponin I (cTnI) is a low-abundance biomarker useful for diagnosing patients for myocardial injury. In particular, a ratio between phosphorylated and unphosphorylated cTnI may be used as an indicator of patients' risk of suffering myocardial damage. However, normal cTnI levels in healthy people are very low, and thus obtaining baseline cTnI levels is difficult. Conventional techniques for measuring such low levels of cTnI include non-equilibrium isoelectric focusing, mass spectrometry, and phosphate-affinity sodium dodecyl sulfate polyacrylamide gel electrophoresis ("SDS-PAGE"). These conventional techniques, however, are complex, costly, and low in throughput.

BRIEF DESCRIPTION OF THE DRAWINGS

FIG. 3A is a plan view of another electrophoresis device suitable for the analysis system in FIG. 1A in accordance with embodiments of the present technology.

FIG. 3B is a cross-sectional view of a portion of the electrophoresis device in FIG. 3A in accordance with embodiments of the present technology.

FIG. 4A is a plan view of another electrophoresis device suitable for the analysis system in FIG. 1A in accordance with embodiments of the present technology.

FIG. 4B is a cross-sectional view of a portion of the electrophoresis device in FIG. 4A in accordance with embodiments of the present technology.

DETAILED DESCRIPTION

Figure 1A:
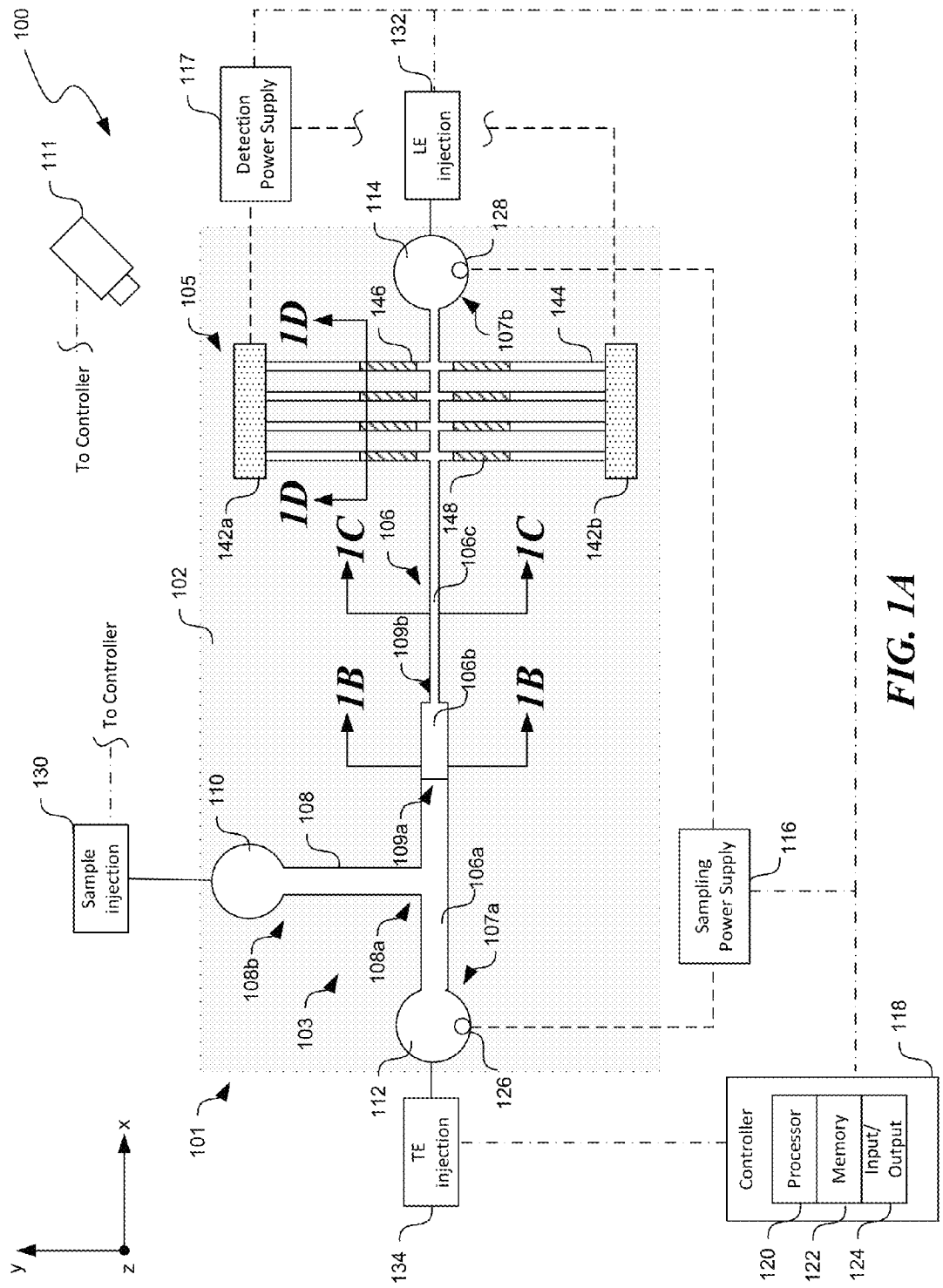
FIG. 1A is a partially schematic diagram of an analysis system in accordance with embodiments of the present technology.

Various embodiments of analysis systems, electrophoresis devices, and associated methods of analysis are described below. As used herein, the term "electrophoresis" generally refers to separating electrically charged particles in a sample based on mobility of the particles relative to a fluid under the influence of an electric field. When the separated particles are positively charged, the separation process is generally referred to as "cataphoresis." Conversely, when the separated particles are negatively charged, the separation process is generally referred to as "anaphoresis." Without being bound by theory, it is believed that different charged particles can migrate at different speeds (commonly referred to as electrophoretic mobility) relative to a fluid in an electric field. The charged particles may have different charge polarity, charge state, particle size, and/or other characteristics. As a result, the charged particles separate from one another during migration in the fluid (e.g., a solvent or buffer solution). The separated charged particles may then be collected and further analyzed for identification and/or abundance. The term "microchannel" generally refers to a channel with a hydraulic diameter below about 1 millimeter.

Also used herein, the term "isotachophoresis" ("ITP") generally refers to an electrophoresis technique in which a sample is introduced between a leading electrolyte ("LE") and a terminating electrolyte ("TE") before an electrical field is applied. The LE has a leading ion with an electrophoretic mobility greater than any charge particles of interest in the sample. The TE has a trailing ion with an electrophoretic mobility lower than any charge particles of interest in the sample. After an electric field is applied, charge particles in the sample separate from one other while the sample is moving along with and between the LE and TE in a channel. After reaching corresponding equilibrium concentrations (i.e., in peak mode), the separated charged particles form distinct volumes or "stacks" in the channel with sharp boundaries between adjacent stacks. The separated particles are stacked in order of respective electrophoretic mobility values with the fastest proximate the leading ion.

As discussed above in the Background section, detecting dilute components of a sample can be challenging. The inventors have recognized that by applying ITP in a microchannel with cross-sectional area reductions, low concentration components (e.g., phosphorylated and un-phosphorylated cTnI) can be separated and substantially concentrated (e.g., by a factor of about 10,000 or greater). The inventors have also recognized that a detection section (e.g., having a cross-linked polymeric matrix, a silica monolith, or a ceramic monolith) may be coupled to the microchannel to form a compact, effective, and low cost diagnostic device. Certain embodiments of analysis systems, electrophoresis devices, and methods of analysis in accordance with the present technology are discussed below. However, a person skilled in the relevant art will understand that the technology may have additional embodiments, and that the technology may be practiced without several of the details of the embodiments described below with reference to FIGS. 1A-9.

FIG. 1A is a partially schematic diagram of an analysis system 100 in accordance with embodiments of the present technology. FIG. 1A also shows a plan view of an electrophoresis device 101. As shown in FIG. 1A, the analysis system 100 can include the electrophoresis device 101 coupled to a sample injection device 130, an LE injection device 132, and a TE injection device 134 (collectively referred to as "injection devices"). The analysis system 100 can also include an extraction power supply 116, a detection power supply 117, and a controller 118 operatively coupled to the electrophoresis device 101. The injection devices can include a syringe, a pump, and/or other suitable devices configured to supply a fluid to the electrophoresis device 101. Even though particular components are shown in FIG. 1A, in other embodiments, the analysis system 100 can also include other suitable components.

As shown in FIG. 1A, the electrophoresis device 101 can include a substrate 102 (shown schematically for clarity) carrying an extraction section 103 in fluid communication with a detection section 105. In one embodiment, the substrate 102 includes a plate or "chip" constructed from poly (methyl methacrylate) ("PMMA"). In other embodiments, the substrate 102 can be constructed with glass, silicon, metals, ceramics, and/or other suitable substrate materials. Though not shown in FIG. 1A, in further embodiments, the electrophoresis device 101 can also include a cover configured to enclose at least the extraction section 103 in the substrate 102. For example, the cover can include a generally flat plate securely fastened to the substrate 102 with glue, mechanical fasteners, welding materials, only pressure, pressure in combination with a solvent, and/or other suitable fasteners. In yet further embodiments, the cover can be generally similar to the configuration of the substrate 102, or may be omitted.

The extraction section 103 is configured to separate and/or concentrate one or more target components in a sample. As shown in FIG. 1A, in the illustrated embodiment, the extraction section 103 includes a first channel 106 in fluid communication with a second channel 108. The first channel 106 includes a first section 106a, a second section 106b, and a third section 106c arranged in series between a first end 107a and a second end 107b. The first channel 106 is coupled to a TE reservoir 112 at the first end 107a, to an LE reservoir 114 at the second end 107b, and to the detection section 105 at the third section 106c. The second channel 108 includes a first end 108a coupled to the first section 106a of the first channel 106 and a second end 108b coupled to a sample reservoir 110.

Figure 1B:
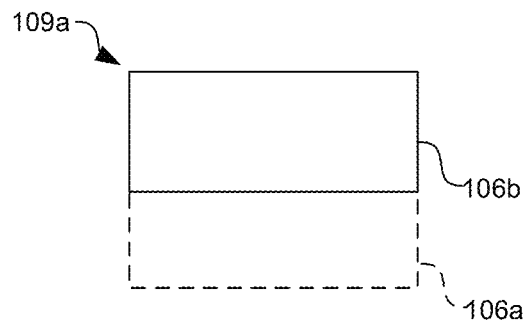
FIGS. 1B-1D are cross-sectional views of a portion of the electrophoresis device in FIG. 1A in accordance with embodiments of the present technology.
Figure 1C:
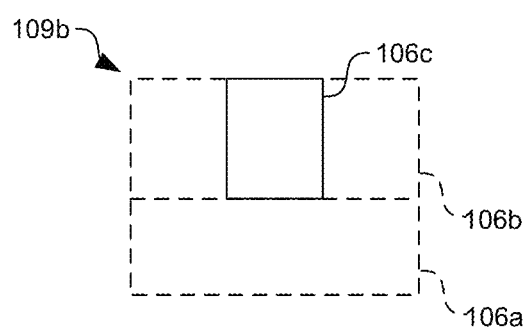

The first channel 106 can include one or more constrictions along the x-dimension. As used herein, the term "constriction" generally refers to a reduction in cross-sectional area along a migration direction. For example, as shown in FIG. 1B, the first section 106a of the first channel 106 has a cross-sectional area that is larger than the second section 106b in a first dimension (e.g., the z-dimension) to form a first constriction 109a. As shown in FIG. 1C, the second section 106b has a cross-sectional area larger than the third section 106c generally in a second dimension (e.g., the y-dimension) to form a second constriction 109b. The first dimension is generally perpendicular or orthogonal to the second dimension.

The cross-sectional area reduction across the first and/or second constrictions 109a and 109b can be by a factor of 2, 3, 4, 5, 10, 100, and/or other suitable values. In certain embodiments, the first and second constrictions 109a and 109b can have the same reduction factor (e.g., 10). In other embodiments, the first and second constrictions 109a and 109b can have different reduction factors. Even though particular configuration of first and second constrictions 109a and 109b is shown in FIGS. 1A-1C, in other embodiments, the electrophoresis device 101 may include other passage configurations, as discussed in more detail below with reference to FIGS. 2-6.

Referring back to FIG. 1A, the analysis system 100 can also include a first electrode 126 and a second electrode 128 electrically coupled to the extraction power supply 116. The first and second electrodes 126 and 128 can include platinum, gold, and/or other suitable types of electrodes. In the illustrated embodiment, the first and second electrodes 126 and 128 are placed in the TE reservoir 112 and the LE reservoir 114, respectively. In other embodiments, the first and second electrodes 126 and 128 can be spaced apart from but electrically coupled to the TE reservoir 112 and the LE reservoir 114, respectively. In further embodiments, the first and second electrodes 126 and 128 can have other suitable configurations.

The detection section 105 is configured to collect, accumulate, and/or otherwise capture the separated and/or concentrated components from the extraction section 103. As shown in FIG. 1A, the detection section 105 includes a plurality of detection channels 144 intersecting the third section 106c of the first channel 106. The detection channels 144 are arranged between a first detection electrode 142a and a second detection electrode 142b, which are electrically coupled to the detection power supply 117. Even though the detection section 105 is shown in FIG. 1A as having four detection channels 144, in other embodiments, the detection section 105 may include any other suitable number of detection channels.

Figure 1D:
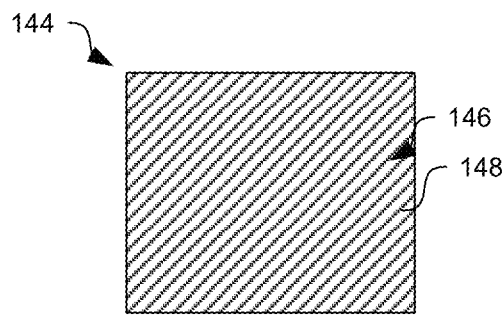

In the illustrated embodiment, the individual detection channels 144 in the detection section 105 include a detection site 146. For example, as shown in FIG. 1D, the detection channel 144 can include a PMMA microchannel, and the detection site 146 can include a polymethacrylic acid (or other polymeric material) matrix (commonly referred to as a "brush") 148 locally grated to the PMMA microchannel via photochemical immobilization. The polymethacrylic acid brush may be placed at any desired locations along the detection channels 144. For example, the detection site 146 may be spaced apart from the first channel 106 or may abut the first channel 106. In other embodiments, at least one of the microchannels 144 does not include a detection site 146. In further embodiments, none of the microchannels 144 include detection sites 146. In yet further embodiments, at least one of the microchannels 144 can include more than one detection sites 146.

In certain embodiments, the detection section 105 may also include a marker, an antibody, an enzyme, and/or other suitable recognition element (not shown). The recognition element may be configured to selectively bind to, react with, and/or otherwise specifically interact with a target of the collected components to impart a detectable event (e.g., optical, electrochemical, etc.) for identifying, quantifying, and/or otherwise providing indication of the target. For example, the detection section 105 can include a UV fluorescent material (e.g., Pacific Blue C5-maleimide) configured to react with a target component (e.g., cTnI). After combining with the target component, the recognition element can produce a fluorescent glow under excitation. An average intensity of the fluorescent glow can be proportional and/or otherwise related to a concentration of the target component. In further embodiments, the detection section 105 can include other suitable identifiers, quantifiers, and/or other suitable component.

Referring back to FIG. 1A, the extraction power supply 116 and the detection power supply 117 can individually include a direct current source, a transformer, a rectifier, and/or other suitable electrical components configured to supply a voltage to the extraction section 103 and the detection section 105, respectively. Even though the extraction power supply 116 and the detection power supply 117 are shown as separate components in FIG. 1A, in other embodiments, a single power supply (not shown) may be provide power to both the extraction section 103 and the detection section 105.

The detector 111 is configured to identify, quantify, and/or otherwise measure the components of the sample collected in the detection section 105. In the illustrated embodiment, the detector 111 includes a camera configured to measure a fluorescent intensity of the collected components in the sample. In other embodiments, the detector 111 can also include an immuno-affinity assay, a capillary-zone electrophoresis analyzer, an isoelectric focusing analyzer, a gel electrophoresis analyzer, a mass spectrometry analyzer, an SDS-PAGE analyzer, and/or other suitable types of analyzer. In further embodiments, the detector 111 may be omitted, and the collected components of the sample may be analyzed and/or processed with other suitable techniques.

The controller 118 is configured to control operation of the analysis system 100. The controller 118 can include a processor 120 coupled to a memory 122 and an input/output component 124. The processor 120 can include a microprocessor, a field-programmable gate array, and/or other suitable logic devices. The memory 122 can include volatile and/or nonvolatile computer readable media (e.g., ROM; RAM; magnetic disk storage media; optical storage media; flash memory devices, EEPROM, and/or other suitable non-transitory storage media) configured to store data received from, as well as instructions for, the processor 120. The input/output component 124 can include a display, a touch screen, a keyboard, a track ball, a gauge or dial, and/or other suitable types of input/output devices configured to accept input from and/or provide output to an operator.

In certain embodiments, the controller 118 can include a computer operatively coupled to the other components of the analysis system 100 via a hardwire communication link (e.g., a USB link, an Ethernet link, an RS232 link, etc.). In other embodiments, the controller 118 can include a logic processor operatively coupled to the other components of the analysis system 100 via a wireless connection (e.g., a WIFI link, a Bluetooth link, etc.). In further embodiments, the controller 118 can include an application specific integrated circuit, a system-on-chip circuit, a programmable logic controller, and/or other suitable computing frameworks.

Several embodiments of the analysis system 100 can be used to separate, concentrate, detect, and/or quantify one or more target components in a sample. In certain embodiments, the controller 118 can cause the LE injection device 132 to inject an LE carried by a fluid (e.g., a buffer solution) into the LE reservoir 114 and the first channel 106 until the injected fluid substantially fills the first and second channels 106 and 108. Subsequently, the controller 118 can cause the sample injection device 130 to inject a sample (e.g., a blood sample) into the sample reservoir 110. The injected sample can then substantially fill the first section 106a of the first channel 106 and the TE reservoir 112 by displacing a portion of the LE. Then, the controller 118 can cause the TE injection device 134 to inject a TE into the TE reservoir 112.

The controller 118 can then issue instructions to the extraction power supply 116 to supply a voltage (e.g., about 100 volts to about 400 volts) to the first and second electrodes 126 and 128. Under the influence of the applied voltage, the LE, sample, and TE migrate along the x-dimension in the first channel 106. As a result, components of the sample are separated by ITP to form distinctive stacks based on electrophoretic mobility of individual components. As such, the first channel 106 may also be referred to generally as an "extraction" or "separate" channel.

As shown in FIG. 1A, the applied voltage also forces the migrating sample to migrate through the first constriction 109a and the second constriction 109b while components of the sample are separated by ITP. The inventors have recognized that by forcing the sample to migrate through the first and second constrictions 109a and 109b, components of the sample can be substantially concentrated. Without being bound by theory, it is believed that as the cross-sectional area of the first channel 106 is decreased, concentrations of sample components can be increased proportionally when ITP zones are in peak mode as follows:

$$c_i = \frac{M_i}{w_i A} \quad \text{Equation 1}$$

where $c_i$ is the concentration of a sample component i, $M_i$ is a total mass or molar load of component i, $w_i$ is a peak width of species i, and A is a cross-sectional area of the first channel 106. As shown in Equation 1, the concentration of a sample component $c_i$ is inversely proportional to the cross-sectional area A of the first channel 106. As a result, a reduction in the cross-sectional area A of the first channel 106 can result in an increase in the concentration of the sample component $c_i$.

Subsequently, the controller 118 can issue instructions to the extraction power supply 116 to remove the supplied voltage from the first and second electrodes 126 and 128. In one embodiment, the extraction power supply 116 removes the supplied voltage after a preset amount of time, which may be determined by performing test runs to derive time required for the target components to reach peak mode. In other embodiments, the controller 118 can monitor stack formation of the sample in the first channel 106 in real time with the detector 111. When the stacks are substantially constant (e.g., relatively constant peak width, fluorescent intensity, etc.), the controller 118 can issue instructions to remove the supplied voltage. In further embodiments, the controller 118 may remove the supplied voltage based on a combination of a preset amount of time and real time monitoring, and/or other suitable criteria.

The detection sections 105 can then collect and/or analyze the separated and/or concentrated target components (e.g., phosphorylated and unphosphorylated cTnI) in stacks. Without being bound by theory, it is believed that the formed stacks in the first channel 106 are relatively stable within a short period of time (e.g., 10 minutes) after power is removed from the first and second electrodes 126 and 128. However, given longer periods (e.g., beyond 10 minutes), the stacks of separated components may migrate toward one another and remix. As a result, after removing power from the first and second electrodes 126 and 128, the detection section 105 can readily collect and/or analyze the separated and/or concentrated target components.

In the illustrated embodiment, the controller 118 issues instructions to the detection power supply 117 to provide a voltage to the detection section 105. Under the influence of the applied electrical voltage, the separated target components migrate into the detection channels 144 in the detection section 105 and, in certain embodiments, attach to a detection site 146 (e.g., a polymethacrylic acid brush) via van der Waal forces, hydrogen bonding, and/or other suitable attachment mechanisms. In other embodiments, the target components in the sample may be marked (e.g., with a UV fluorescent marker) before the sample is injected into the extraction section 103. In further embodiments, the target components may combine with markers contained in the detection section 105. In yet further embodiments, the target components may be otherwise suitably collected.

The detector 111 then detects and measures a characteristic of the separated components. In one embodiment, the detector 111 includes a camera configured to record a position and fluorescent intensity of various stacks in the detection section 105. In other embodiments, the detector 111 can perform other suitable analysis on the collected target components. Based at least in part on such information, the controller 118 can calculate an initial concentration of the target components as follows.

Figure 8:
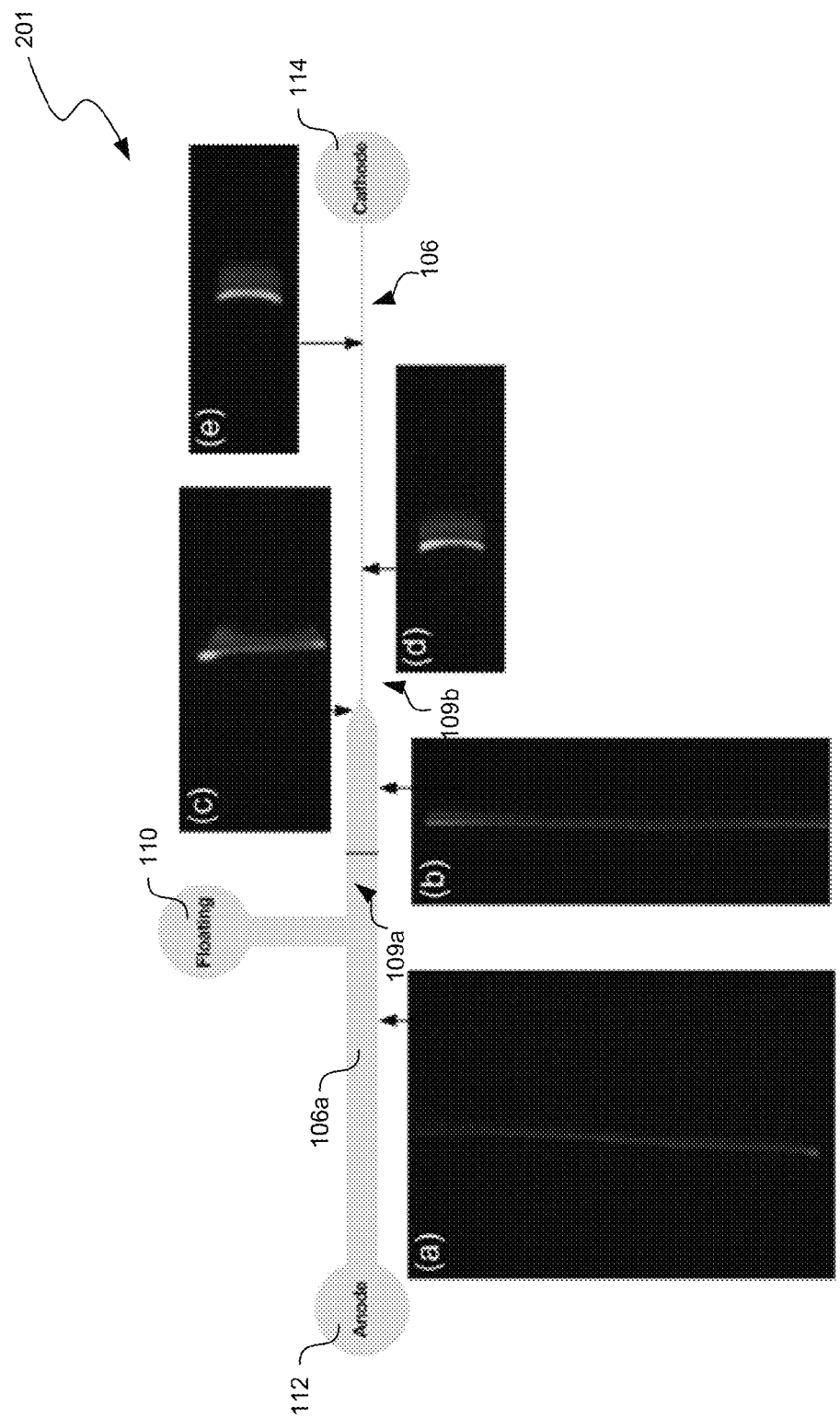
FIG. 8 shows stacking of labeled cTnI at different locations in the electrophoretic device in FIG. 6 during experiments conducted in accordance with embodiments of the present technology.

First, electropherograms may be constructed by plotting distance relative to a field of view of the detector 111 versus average intensity over entire width of the first channel 106 for a target component. An example electropherogram is shown in FIG. 8 for illustration purposes. Then, a moment analysis may be performed on data collected from the electropherogram to obtain information of peak width for the target component. Without being bound by theory, it is believed that the $n^{th}$ moment converted from temporal to spatial moments is given by:

$$m_n = \int_a^b m_{n,i}\, dx = \int_a^b I(x) \cdot x^n\, dx \qquad \text{Equation 2}$$

where I(x) is an intensity value, x is a spatial position, a and b are limits of integration based on the field of view of the detector 111, and $m_{n,i}$ was calculated using the trapezoidal rule at distinct position values such that:

$$\int_a^b m_{n,i}\, dx = \sum_i \frac{1}{2}(I(x_{i+1}) \cdot x_{i+1}^n + I(x_i) \cdot x_i^n)(x_{i+1} - x_i).$$

The variance ($\sigma^2$) is defined by the following relationship:

$$\sigma^2 = \frac{\int_a^b I(x) \cdot (x - x_m)^2\, dx}{\int_a^b I(x) \cdot dx} \qquad \text{Equation 3}$$

where $x_m$ is the mean location of mass. The variance can then be derived using $n^{th}$ moments to the following equation:

$$\sigma^2 = \frac{m_2}{m_0} - \left(\frac{m_1}{m_0}\right)^2 \qquad \text{Equation 4}$$

The resulting peak width ($W_i$) for each peak is then given by $$W_i = 4\sigma \qquad \text{Equation 5}$$

where $\sigma$ is the standard deviation. The concentration of the target component can then be calculated from Equation 1 where Wi is the peak width of target component calculated from Equation 5.

Figure 2:
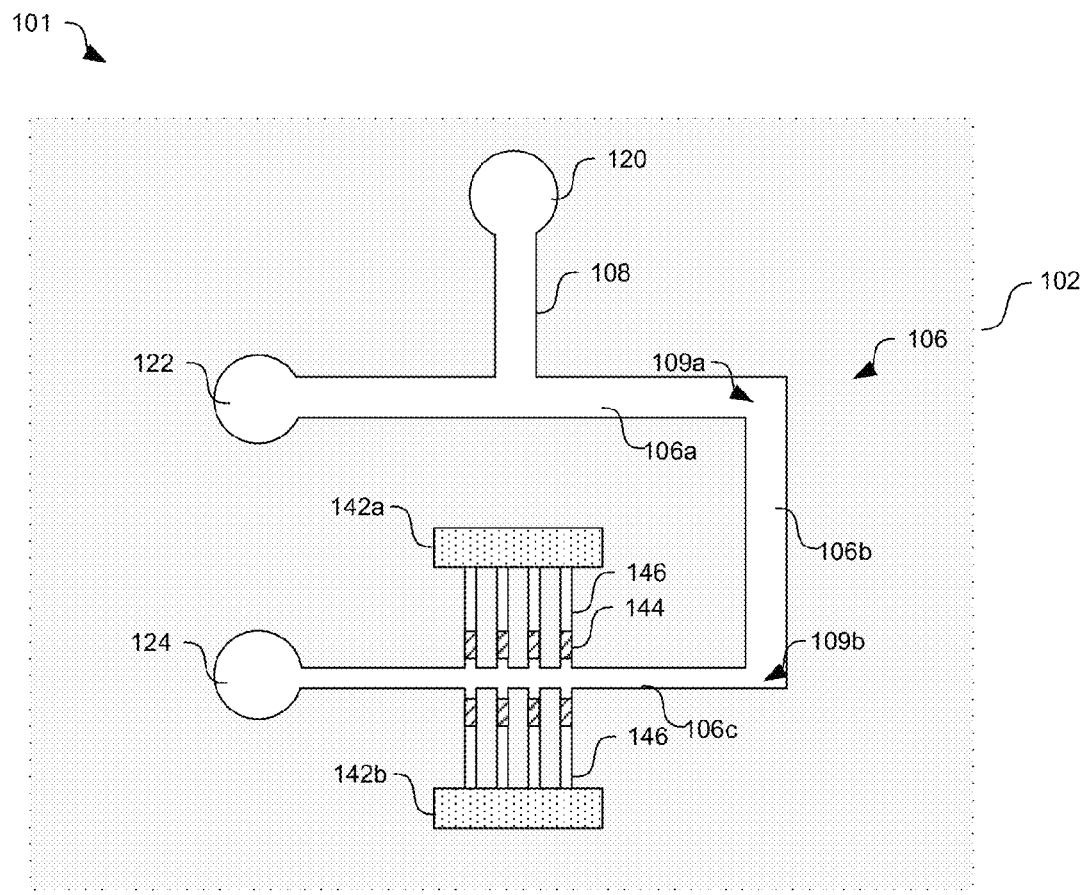
FIG. 2 is a plan view of another electrophoresis device suitable for the analysis system in FIG. 1A in accordance with embodiments of the present technology.

The electrophoresis device 101 shown in FIG. 1A has a generally linear first channel 106. In other embodiments, the electrophoresis device 101 can also include non-linear channels. For example, FIG. 2 is a plan view of another electrophoresis device 101 suitable for the analysis system in FIG. 1A in accordance with embodiments of the present technology. As shown in FIG. 2, the electrophoresis device 101 can include generally similar components as that in FIG. 1A except that the first section 106a, the second section 106b, and the third section 106c of the first channel 106 are arranged generally in a "U" shape. In other embodiments, sections of the first channel 106 can also form a "Z" shape, an "L" shape, an "S" shape, or other suitable shapes.

Even though the first channel 106 in FIGS. 1A-2 is shown to have consecutive and discrete reductions in cross-sectional area, in other embodiments, the first channel 106 can also have a single two-dimensional reduction in cross-sectional area. FIG. 3A is a plan view and FIG. 3B is a cross-sectional view of another electrophoresis device 101 suitable for the analysis system 100 in FIG. 1A in accordance with embodiments of the present technology. In FIGS. 3A and 3B and in other figures, certain components of the electrophoresis device 101 are omitted for clarity. As shown in FIGS. 3A and 3B, in certain embodiments, the electrophoresis device 101 includes a single constriction 109 with a reduction in cross-sectional area in both the z-dimension and the y-dimension. As a result, the second section 106b can be generally concentric to the first section 106a. FIG. 4A is a plan view and FIG. 4B is a cross-sectional view of another electrophoresis device 101 with a single constriction 109 except that the first channel 106 includes a tapered portion 111 between the first section 106a and the second section 106b.

Figure 5A:
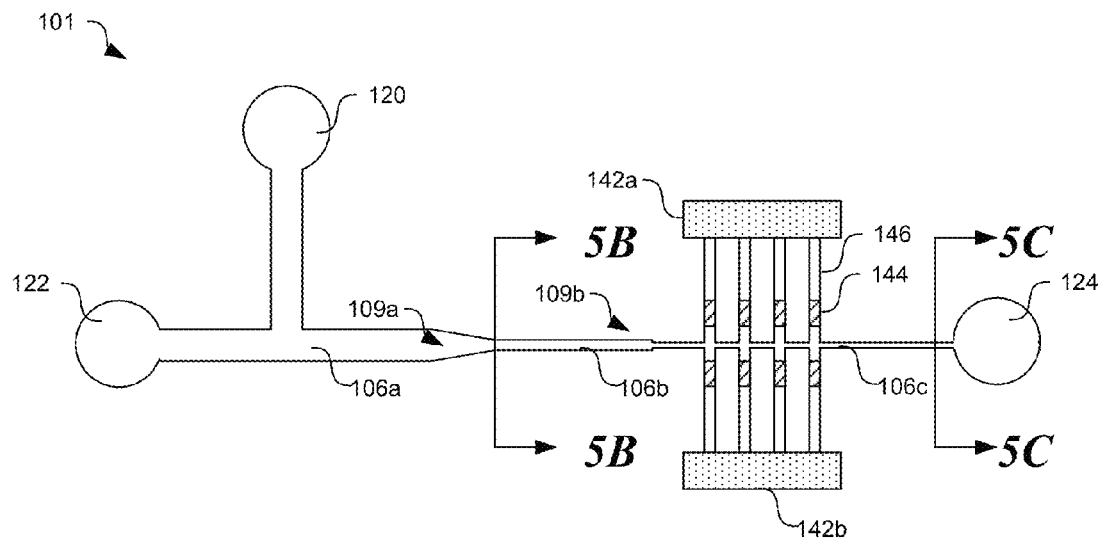
FIG. 5A is a plan view of another electrophoresis device suitable for the analysis system in FIG. 1A in accordance with embodiments of the present technology.
Figure 5B:
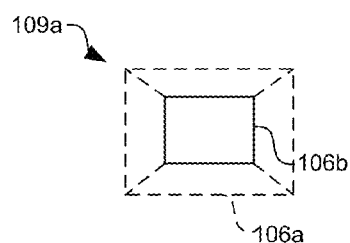
FIGS. 5B and 5C are cross-sectional views of a portion of the electrophoresis device in FIG. 5A in accordance with embodiments of the present technology.
Figure 5C:
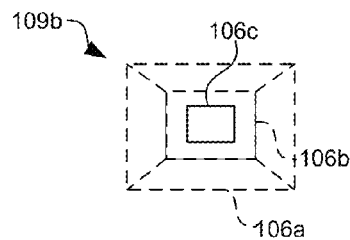

In other embodiments, the electrophoresis device 101 can also include a plurality of constrictions individually having two-dimensional reduction in cross-sectional area. For example, FIG. 5A is a plan view and FIGS. 5B and 5C are cross-sectional views of another electrophoresis device 101 with first and second constrictions 109a and 109b. The first constriction 109a is generally similar to that shown in FIG. 4A, and the second constriction 109b is generally similar to that shown in FIG. 3A. In further embodiments, the electrophoresis device 101 can also include three, four, or any suitable number of constrictions with cross-sectional area reduction in one dimension or two-dimensions.

Figure 6:
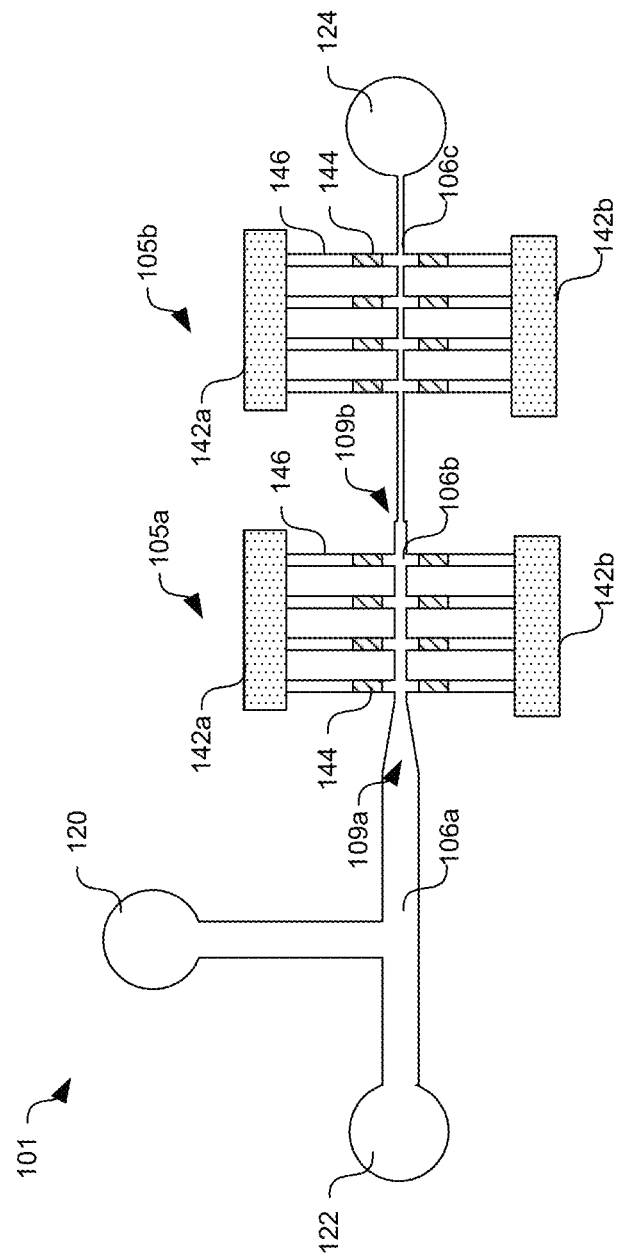
FIG. 6 is a plan view of an electrophoresis device with multiple detection sections in accordance with embodiments of the present technology.

Even though the electrophoresis device 101 is shown in FIGS. 1A-5B as having a single detection section 105, in other embodiments, the electrophoresis device 101 can also include multiple detection sections 105 arranged along the first channel 106. For example, FIG. 6 is a plan view of an electrophoresis device 101 with multiple detection sections in accordance with embodiments of the present technology. As shown in FIG. 6, the electrophoresis device 101 includes a first detection section 105a and a second detection section 105b (collectively referred to as "detection sections 105"). The first detection section 105 is downstream of the first constriction 109a. The second detection section 105b is downstream of the second constriction 109b along the first channel 106. In the illustrated embodiment, the first and second detection sections 105a and 105b are generally similar to each other in structure and in function. In other embodiments, the first and second detection section 105a and 105b may be different from each other.

In certain embodiments, the first and second detection sections 105a and 105b may be configured to detect and/or analyze components at different concentration levels in a sample. For example, as shown in FIG. 6, the first detection section 105a may be configured to detect a first component with a first concentration (e.g., at about ppm level). The second detection section 105b may be configured to detect a second component with a second concentration (e.g., about ppb level) that is lower than the first concentration. As a result, multiple target components may be detected and/or analyzed in one operation, and thus reducing costs and operational complexity. In further embodiments, the electrophoresis device 101 can include three, four, or any other suitable number of detection sections.

Certain experiments were conducted to test the efficacy of ITP analysis in a microchannel with reduction in cross-sectional area. In the experiments, an electrophoresis device generally similar to that shown in FIG. 1A was used. As discussed in more detail below, by performing ITP in a cross-sectional area reducing microchannel, concentration factors greater than 10,000 were achieved.

Chemicals Used In Experiments

R-phycoerythrin (PE, MW=240,000 Da) was purchased from Molecular Probes of Eugene, Oreg. Potassium acetate, polyvinylpyrrolidone K-90 (PVP, MW=360,000 Da), urea, terrific broth (TB), carbenicillin, Triton X-100, sodium azide ($NaN_3$), phenylmethylsulphonylfluoride (PMSF), benzamidine, ammonium sulfate (($NH_4$)$_2SO_4$), citric acid, dithiothreitol (DTT), ethylenediaminetetraacetic acid, β-mercaptoethanol sodium chloride (NaCl), potassium chloride (KCl), potassium phosphate ($KH_2PO_4$), and disodium phosphate ($Na_2HPO_4$) were purchased from Sigma-Aldrich of St. Louis, Mo. Pacific Blue™ C5-maleimide was purchased from Molecular Probes of Carlsbad, Calif.

Human cTnI (HcTnI) encoding gene was subcloned into expression vector pET3d. The resultant plasmid pET3d-hcTnI was transformed into OneShot® BL21 Star™ (DE3) Chemically Competent *E. coli* cells. The cells were grown on Luria Broth (LB) medium agar plates supplemented with 50 μg/mL of carbenicillin at 37° C. overnight. Several colonies were picked up and inoculated into 15 mL LB-carbenicillin liquid medium and shaken at 37° C. until $OD_{600}$ is up to 0.8~1. The pre-culture was inoculated into 2 L TB medium with 50 μg/mL carbenicillin. After shaking at 37° C. for 18 hours, the cells were spun down at 7,000×g for 10 min.

Preparation of cTnI

Cell pellets were suspended in a carboxy methyl (CM) buffer (6 M urea, 30 mM citric acid, 1 mM EDTA, and 1 mM DTT) with 0.01% Triton X-100, 0.01% $NaN_3$, 2 mM PMSF and 2 mM benzamidine and sonicated with a Misonix Sonicator® 3000 Ultrasonic Liquid Processor provided by Misonix Inc., Farmingdale, N.Y., on ice. The crude lysate was clarified by centrifugation at 40,000 G for 30 min. The supernatant was brought to 30% and 60% saturation with ($NH_4$)$_2$SO$_4$ sequentially, followed by stirring at 4° C. for 1 hour, and spun down at 28,000 G for 20 min. The supernatant was decanted and the pellet was re-suspended in 50 mL CM buffer. The solution was dialyzed against 1 L CM buffer overnight at 4° C. to remove residual ($NH_4$)$_2$SO$_4$. Next, the dialyzed and clarified supernatant was loaded onto an equilibrated CM sepharose (GE) column and an ÄKTA™ FPLC™ System (GE) was used to run gradient elution of NaCl concentration increasing from 0 to 0.3 M. The potential cTnI peak fractions were collected and SDS-PAGE was performed to evaluate the purity of the cTnI fractions.

Labeling of cTnI

Phosphate buffer saline (PBS) was prepared using NaCl, KCl, $Na_2HPO_4$, and $KH_2PO_4$ to pH 7.4, and 1.5 mL of purified cTnI was dialyzed three times in 1 L solutions of PBS 7.4 with 4 M urea for at least 8 hours at 4° C. in a 10,000 MWCO Slide-A-Lyzer Dialysis Cassette provided by Piercenet of Rockford, Ill. After dialysis, the cTnI was labeled with Pacific Blue™ C5-maleimide according to the manufacturer's instructions. Pacific Blue™ C5-maleimide is a UV fluorescent, thiol-reactive probe that readily reacts with the two cysteine groups on the cTnI molecule. A 10× molar excess of dye was mixed with the cTnI and allowed to react at 4° C. overnight. An excess of β-mercaptoethanol was added to quench the reaction. The labeled cTnI was again dialyzed as mentioned previously to remove excess dye. A Beckman Coulter DU 730 UV/Vis spectrophotometer provided by Beckman Coulter, Inc., of Brea, Calif., was used to determine the final protein concentration and the degree of labeling. The final protein concentration of cTnI was 0.46 mg/mL and the degree of labeling was about 2. The cTnI isoelectric point was checked by running isoelectric focusing PAGE (IEF-PAGE).

Electrolyte Solutions

An LE solution was prepared by adjusting pH of 20 mM potassium acetate solution to pH 4.5 with 10% (v/v) acetic acid. A TE solution includes 10 mM acetic acid at pH 3.8. PVP at 1% (w/v) was added to both LE and TE in order to suppress electro-osmotic migration. PE and labeled cTnI stock solutions were diluted in LE solution to concentrations of 4.0 μg/mL and 2.3 μg/mL, respectively. All electrolyte solutions were made up using nano-pure water. Electrolyte solutions were degassed with a vacuum pump.

Experimental Setup

Figure 7:
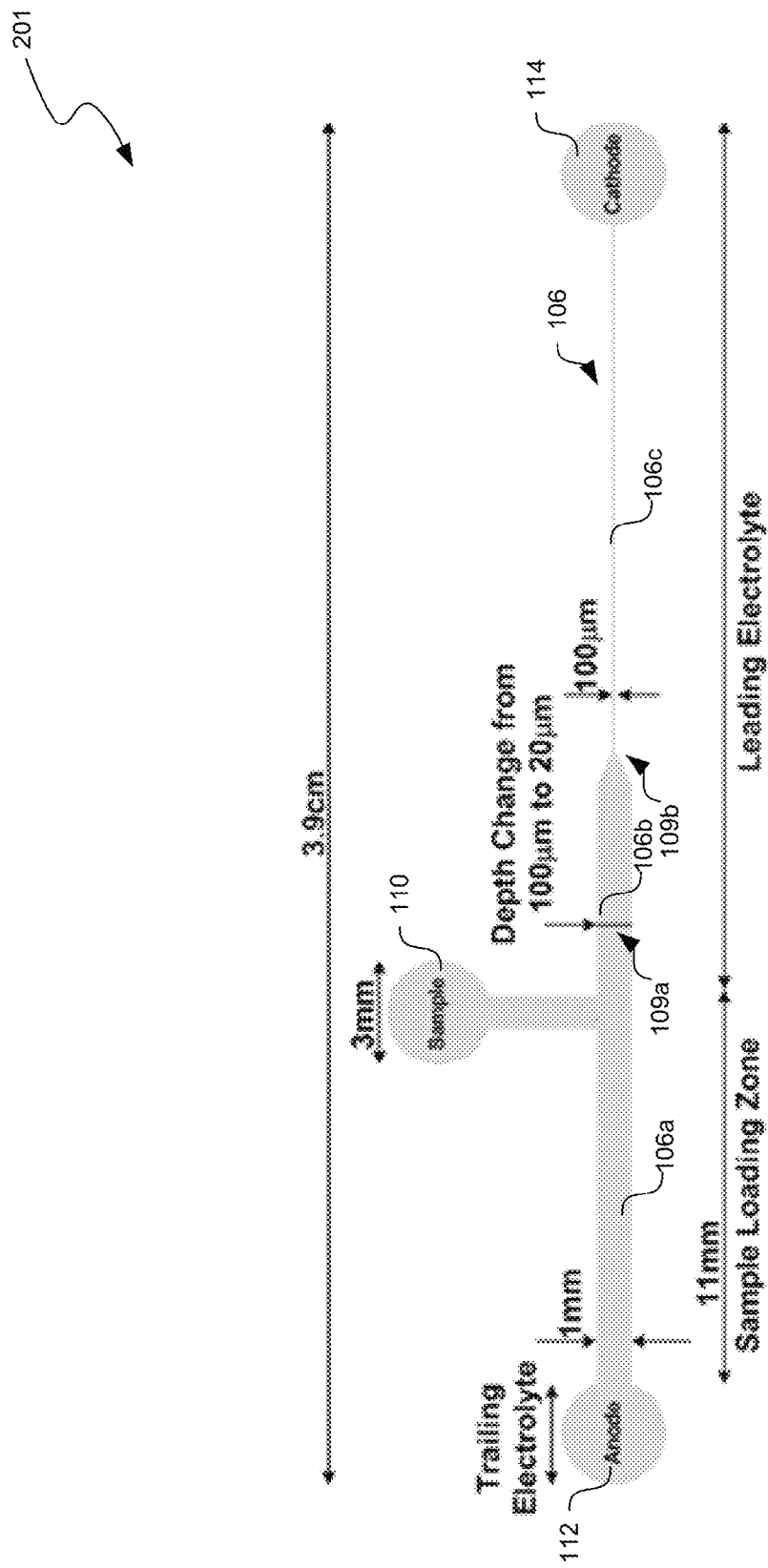
FIG. 7 is a plan view of an electrophoresis device showing dimensions for use in experiments in accordance with embodiments of the present technology.

FIG. 7 is a plan view of an electrophoresis device 201 used in the experiments with certain dimensions shown. As shown in FIG. 7, the electrophoresis device 201 is generally similar to the electrophoresis device 101 shown in FIG. 1A. As such, identical reference numbers identify similar elements or acts.

During testing, the electrophoresis device 201 was initially filled with the LE from the cathode reservoir 114 to the anode reservoir 112 using a 3 mL disposable syringe. Next, diluted PE and labeled cTnI in LE were introduced into the sample reservoir 110 and filled towards the anode reservoir 112 so that LE occupying the region between the sample reservoir 110 and anode reservoir 112 was washed out of the anode reservoir 112. At this point, the sample solution occupied the region between the sample reservoir 110 and the anode reservoir 112. The total mass load ($M_i$) of both PE and cTnI injected into the passage may be calculated by multiplying the initial concentration by the volume of the sample loading zone (1.1 μL). Next, the anode reservoir 112 was rinsed several times with TE and then filled with TE.

The filled electrophoresis device 201 was placed underneath a 5× objective lens of a Leica DM 2000 fluorescence microscope equipped with a DFC310 digital color camera provided by Leica Microsystems Inc., Bannockburn, Ill. The camera was controlled with the provided Leica Application Suite (LAS) V3.6 software to collect images of fluorescent proteins as the proteins migrated through the first channel 106 via ITP. The exposure time was set to 67.7 millisecond and the gain was set to 4.1×. The fluorescent proteins were excited with a Leica Microsystems EL 6000 light source using an A type filter cube. Platinum electrodes were submerged in the anode reservoir 112 and cathode reservoir 114 while the sample reservoir 110 was left to float.

Initially, the anode reservoir 112 was grounded and the cathode reservoir 114 was set to 400 V. After the proteins migrate from the first section 106a into the second section 106b, the voltage on the cathode reservoir 114 was reduced to 100 V. Representative images at the end of each experiment were collected. Electropherogram of the images were obtained for further analysis.

Results and Discussion

Potassium ion was chosen as the LE ion. Hydronium ion was chosen as the TE ion. The initial mass load ($M_i$) was calculated from the following equation $$M_i = c_i^0 \cdot L \cdot A$$

where $c_i^0$ is the initial concentration of protein i (4.0 μg/mL and 2.3 μg/mL for PE and cTnI, respectively), L is the length of sample loading zone (11 mm), and A is the cross-sectional area of the first channel 106 (0.1 mm$^2$). Thus, the total mass for PE and cTnI was 4.40 and 2.53 ng, respectively.

FIG. 8 shows stacking of labeled cTnI at different locations in the electrophoretic device 201 in FIG. 6 during experiments. As shown in FIG. 8, the proteins were not visualized until just before first constriction 109*a*. At the running pH, cTnI ran ahead of PE because cTnI had a higher effective electrophoretic mobility. The proteins continued to collect mass through the sample loading zone and the intensity of the fluorescence increased as they migrated through the first constriction 109*a*. Prior to the second constriction 109*b*, the voltage on the cathode was reduced from 400 to 100V. An image was collected prior to protein bands migration into the cathode reservoir 114 clearly demonstrating ITP stacking of labeled cTnI and PE into nearly pure and distinct zones.

Figure 9:
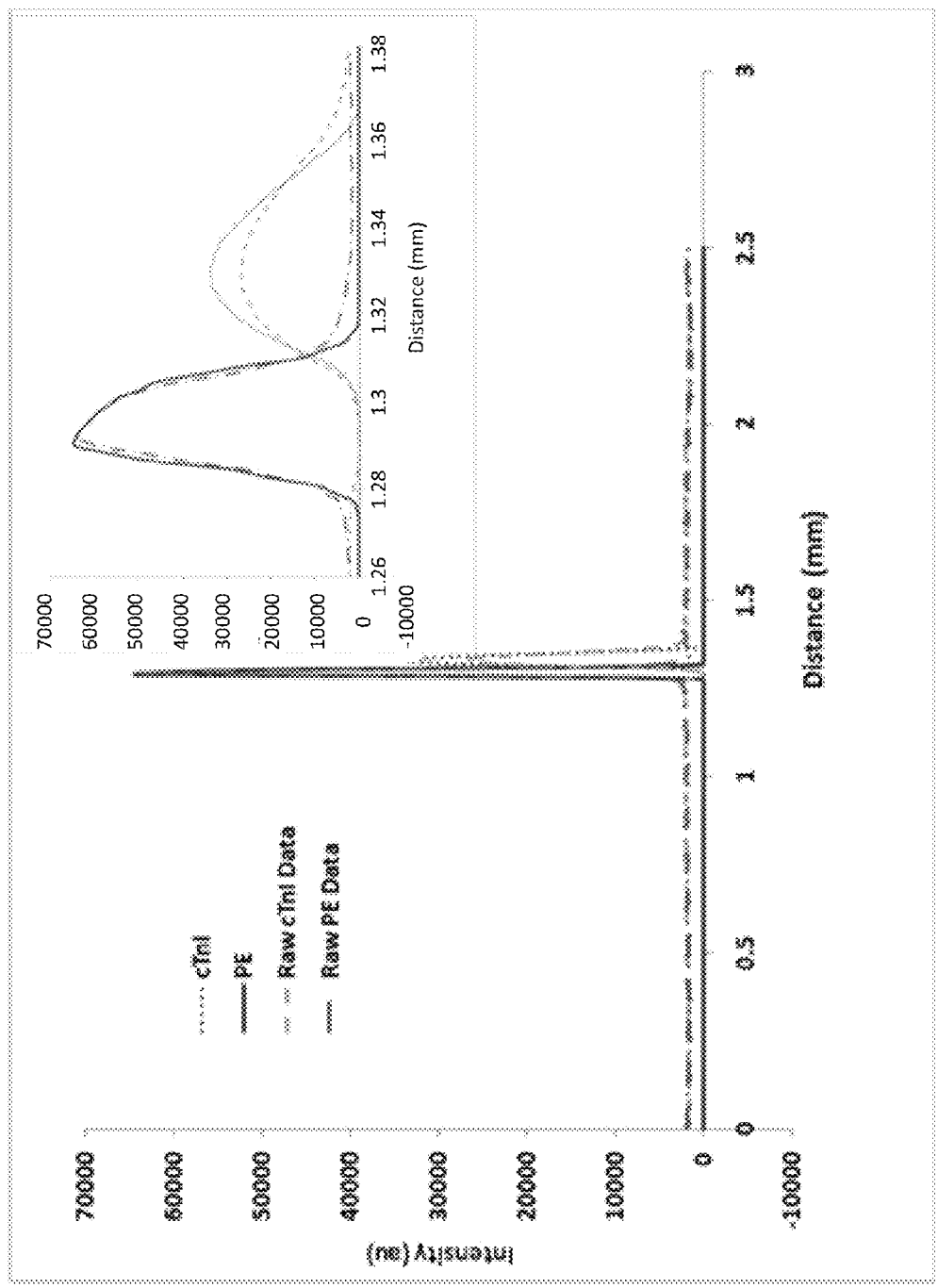
FIG. 9 is an electropherogram of test results based on experiments conducted in accordance with embodiments of the present technology.

After several runs, electropherograms were obtained by plotting distance (mm) relative to the field of view of the camera versus average intensity over the entire width of the first channel 106 for each protein. FIG. 9 shows an example electropherogram including both raw and modified data with an inset showing an enlarged plot of protein peaks. Using moment analysis, the peak width of each protein can be determined from the data. Subsequent concentrations and concentration factors for each protein were then calculated based on the electropherograms.

A summary of the experimental peak widths determined from the moment analysis, final concentrations from Equation 1, and concentration factors for PE and cTnI are shown in the table below.

| | PE | | | cTnI | | |
|---|---|---|---|---|---|---|
| Trial # | Peak width (μm) | Concentration (mg mL$^{-1}$) | Concentration Factor | Peak width (μm) | Concentration (mg mL$^{-1}$) | Concentration Factor |
| 1 | 30.21 | 72.84 | 18,210 | 50.83 | 24.89 | 10,822 |
| 2 | 35.58 | 62.18 | 15,545 | 51.21 | 24.70 | 10,739 |
| 3 | 29.45 | 74.70 | 18,675 | 46.93 | 26.96 | 11,722 |
| Average | 31.68 | 69.91 | 17,477 | 49.66 | 25.52 | 11,094 |
| St. Dev. | 3.23 | 6.76 | 1,689 | 2.37 | 1.25 | 545 |

As clearly shown in the table above, an average concentration factor of 17,477 was achieved in three trials.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. An electrophoresis device, comprising:
a first electrode having a first polarity;
a second electrode having a second polarity opposite the first polarity;
a substrate including
a sample reservoir configured to store a sample having a target component;
an extraction channel in fluid communication to the sample reservoir, the extraction channel having a first section with a first cross-sectional area and a second section with a second cross-sectional area between a first end and a second end, the first end being electrically coupled to the first electrode and the second end being electrically coupled to the second electrode, wherein the first cross-sectional area is greater than the second cross-sectional area in a first dimension and in a second dimension generally orthogonal to the first dimension; and
a detection channel in fluid communication with the second section of the extraction channel, the detection channel having a detection site configured to capture the target component in the extraction channel, wherein the detection site includes a cross-linked polymeric matrix carrying at least one of a marker, an anti-body, or an enzyme configured to react with the target component.

2. The electrophoresis device of claim 1 wherein:
the extraction channel further includes an intermediate section with an intermediate cross-sectional area between the first section and the second section;
the first cross-sectional area is greater than the intermediate cross-sectional area;
the intermediate cross-sectional area is greater than the second cross-sectional area;
a first reduction from the first cross-sectional area to the intermediate cross-sectional area is in a first dimension;
a second reduction from the intermediate cross-sectional area to the second cross-sectional area is in a second dimension different than the first dimension;
the second dimension is generally orthogonal to the first dimension;
the extraction channel is a first extraction channel; and
the electrophoresis device further includes
a second extraction channel in fluid communication with the first section of the first extraction channel;
a first reservoir proximate the first end, the first reservoir being configured to store a trailing electrolyte;
a second reservoir proximate the second end, the second reservoir being configured to store a leading electrolyte;
the target component has an electrophoretic mobility higher than that of the trailing electrolyte and lower than that of the leading electrolyte;
the detection channel includes a microchannel having a first side and a second side; and
the electrophoresis device further includes a first detection electrode at the first side and a second detection electrode at the second side of the detection channel, the first and second detection electrodes being configured to generate an electrical field that drives the target component into the detection channel from the extraction channel.

3. The electrophoresis device of claim 1 wherein the detection channel includes a microchannel, and wherein the detection site further includes at least one of a silica monolith or a ceramic monolith.

4. The electrophoresis device of claim 1 wherein the detection channel includes a microchannel.

5. The electrophoresis device of claim 1 wherein the cross-linked polymeric matrix includes a polymethacrylic acid brush.

6. The electrophoresis device of claim 1 wherein the detection channel includes a first side and a second side, and wherein the electrophoresis device further includes a first detection electrode at the first side and a second detection electrode at the second side of the detection channel, the first and second detection electrodes being configured to generate an electrical field that drives the target component into the detection channel from the extraction channel.

7. The electrophoresis device of claim 1 wherein a first reduction in the first dimension and a second reduction in the second dimension are generally concomitant with each other.

8. The electrophoresis device of claim 1 wherein:
the extraction channel further includes an intermediate section with an intermediate cross-sectional area between the first section and the second section;
the first cross-sectional area is greater than the intermediate cross-sectional area;
the intermediate cross-sectional area is greater than the second cross-sectional area;
a first reduction from the first cross-sectional area to the intermediate cross-sectional area is in a first dimension; and
a second reduction from the intermediate cross-sectional area to the second cross-sectional area is in a second dimension different than the first dimension, the second dimension being generally orthogonal to the first dimension.

9. A method of analyzing a sample containing an electrolyte, comprising:
sequentially introducing a leading electrolyte, a sample electrolyte, and a trailing electrolyte into a extraction channel carried by a substrate, the extraction channel having a constriction in cross-sectional area;
applying an electrical field to separate components of the sample electrolyte into stacks and to concentrate the separated components by forcing the sample electrolyte to migrate through the constriction in the extraction channel; and
thereafter, removing the applied electrical field and detecting the separated and concentrated components of the sample in a detection channel carried by the substrate, wherein the detection channel includes a detection site, and wherein the method further includes attaching at least one of the separated and concentrated components to the detection site.

10. The method of claim 9 wherein forcing the sample electrolyte to migrate through the constriction includes forcing the sample electrolyte to migrate through a constriction with a first reduction in cross-sectional area in a first dimension and a second reduction in cross-sectional area in a second dimension different than the first dimension, the first and second reductions are generally concomitant.

11. The method of claim 9, wherein the detection site includes a cross-linked polymeric matrix carrying at least one of a marker, an anti-body, and an enzyme configured to react with the target component, and wherein attaching at least one of the separated and concentrated components to the detection site includes attaching at least one of the separated and concentrated components to the cross-linked polymeric matrix carrying at least one of a marker, an anti-body, and an enzyme configured to react with the target component.

12. The method of claim 9, wherein the detection site includes a cross-linked polymeric matrix, and wherein attaching at least one of the separated and concentrated components to the detection site includes attaching at least one of the separated and concentrated components to the cross-linked polymeric matrix.

13. The method of claim 9 wherein detecting the separated and concentrated components includes:
detecting a position and a fluorescent intensity of one of the separated and concentrated components;
plotting distance versus average intensity of the based on the detected position and fluorescent intensity;
calculating an $n^{th}$ moment based on the plotted distance versus average intensity as follows:

$$m_n = \int_a^b m_{n,i}\, dx = \int_a^b I(x) \cdot x^n\, dx$$

where $I(x)$ is an intensity value, x is a spatial position, a and b are limits of integration based on the field of view of the detector, and $m_{n,i}$ was calculated using the trapezoidal rule at distinct position values such that:

$$\int_a^b m_{n,i}\, dx = \sum_i \frac{1}{2}(I(x_{i+1}) \cdot x_{i+1}^n + I(x_i) \cdot x_i^n)(x_{i+1} - x_i)$$

calculating a variance ($\sigma^2$) based on the $n^{th}$ moment as follows:

$$\sigma^2 = \frac{m_2}{m_0} - \left(\frac{m_1}{m_0}\right)^2$$

calculating a peak width ($W_i$) as follows:

$$W_i = 4\sigma$$

where $\sigma$ is the standard deviation; and
based on the calculated peak width ($W_i$), deriving a concentration of one of the separated and concentrated components i as follows:

$$c_i = \frac{M_i}{w_i A}$$

where $c_i$ is the concentration of the target component i, $M_i$ is a total mass or molar load of component i, $w_i$ is the peak width, and A is a cross-sectional area of the extraction channel.

14. The method of claim 9 wherein detecting the separated and concentrated components includes:
detecting a position and a fluorescent intensity of one of the separated and concentrated components;
deriving a peak width ($W_i$) of a stack corresponding to the one of the separated and concentrated components; and
based on the calculated peak width ($W_i$), deriving a concentration of the one of the separated and concentrated components i as follows:

$$c_i = \frac{M_i}{w_i A}$$

where $c_i$ is the concentration of the target component i, $M_i$ is a total mass or molar load of component i, $w_i$ is the peak width, and A is a cross-sectional area of the extraction channel.

15. The method of claim 9 wherein detecting the separated and concentrated components includes:
determining a peak width ($W_i$) of a stack corresponding to one of the separated and concentrated components; and
based on the calculated peak width ($W_i$) and a dimension of the constriction, calculating a concentration of the one of the separated and concentrated components.

16. A method of measuring cardiac troponin I (cTnI) concentration, comprising:

loading an extraction channel on a substrate with a leading electrolyte, a sample containing cTnI, and a trailing electrolyte in sequence between a first end and a second end of the channel;

applying an electrical field between the first and second ends of the channel;

with the applied electrical field, separating phosphorylated and unphosphorylated cTnI components into stacks under isotachophoresis while forcing the sample to migrate through a constriction in the extraction channel;

detecting the separated phosphorylated and unphosphorylated cTnI components in a detection channel on the substrate and in fluid communication with the extraction channel;

monitoring a formation of the stacks in the extraction channel; and removing the applied electrical field after the stacks are substantially constant.

17. The method of claim 16 wherein:

the applied electrical field is a first electrical field; and removing the applied electrical field includes removing the applied first electrical field after a preset amount of time and applying a second electrical field to drive the separated phosphorylated and unphosphorylated cTnI components into the detection channel.

18. The method of claim 16 wherein:

the applied electrical field is a first electrical field;

removing the applied electrical field includes removing the applied first electrical field; and the method further includes
  applying a second electrical field to drive the separated phosphorylated and unphosphorylated cTnI components in the stacks into the detection channel.

19. The method of claim 16 wherein detecting the separated phosphorylated and unphosphorylated cTnI components includes:

detecting a position and a fluorescent intensity of the separated phosphorylated and unphosphorylated cTnI components;

deriving a peak width ($W_i$) of a stack individually corresponding to the separated phosphorylated and unphosphorylated cTnI components; and based on the derived peak width ($W_i$), deriving a concentration of the phosphorylated and unphosphorylated cTnI components i as follows:

$$c_i = \frac{M_i}{w_i A}$$

where $c_i$ is the concentration of the target component i, $M_i$ is a total mass or molar load of component i, $w_i$ is the peak width, and A is a cross-sectional area of the extraction channel.

20. The method of claim 16 wherein detecting the separated phosphorylated and unphosphorylated cTnI components includes:

deriving a peak width ($W_i$) of a stack individually corresponding to the separated phosphorylated and unphosphorylated cTnI components; and based on the derived peak width ($W_i$) and a dimension of the constriction, calculating a concentration of the phosphorylated and unphosphorylated cTnI components.

* * * * *